United States Patent

Weinzierl et al.

[11] Patent Number: 5,820,825
[45] Date of Patent: Oct. 13, 1998

[54] WASTE CONTAINER FOR PORTABLE BLOOD ANALYZER

[75] Inventors: Michael C. Weinzierl, San Diego; Jeffrey Graves, San Clemente, both of Calif.

[73] Assignee: SenDx Medical, Inc., Carlsbad, Calif.

[21] Appl. No.: 650,624

[22] Filed: May 20, 1996

[51] Int. Cl.⁶ ........................................ B01L 3/00
[52] U.S. Cl. .......................... 422/102; 422/58; 422/101; 422/103; 604/333
[58] Field of Search ................... 422/100, 101, 422/102, 103, 104, 58; 604/333, 332, 340; 493/195, 213, 224; 128/156

[56] References Cited

U.S. PATENT DOCUMENTS

| | | | |
|---|---|---|---|
| 3,804,091 | 4/1974 | Nolan et al. | 128/283 |
| 3,952,727 | 4/1976 | Nolan | 128/283 |
| 4,085,751 | 4/1978 | Dodge | 128/275 |
| 4,121,589 | 10/1978 | McDonnell | 128/283 |
| 4,203,445 | 5/1980 | Jessup et al. | 128/283 |
| 4,516,974 | 5/1985 | Davis | 604/333 |
| 4,642,089 | 2/1987 | Zupkas et al. | 604/4 |
| 4,648,523 | 3/1987 | Strock | 220/20.5 |
| 4,737,139 | 4/1988 | Zupkas et al. | 604/4 |
| 4,763,805 | 8/1988 | Strock | 220/85 A |
| 4,786,394 | 11/1988 | Enzer et al. | 204/401 |
| 4,871,439 | 10/1989 | Enzer et al. | 204/401 |
| 4,890,608 | 1/1990 | Steer | 128/156 |
| 5,059,036 | 10/1991 | Richison et al. | 383/61 |
| 5,147,272 | 9/1992 | Richison et al. | 493/195 |
| 5,147,340 | 9/1992 | Lavender | 604/344 |
| 5,254,073 | 10/1993 | Richison et al. | 493/195 |
| 5,279,797 | 1/1994 | Burns et al. | 422/102 |
| 5,372,594 | 12/1994 | Colacello et al. | 604/333 |
| 5,401,264 | 3/1995 | Leise | 604/333 |
| 5,423,782 | 6/1995 | Wolrich | 604/339 |
| 5,542,902 | 8/1996 | Richison et al. | 493/195 |
| 5,549,587 | 8/1996 | Norton | 604/333 |

*Primary Examiner*—Harold Y. Pyon
*Attorney, Agent, or Firm*—Fish & Richardson P.C.

[57] ABSTRACT

A waste container for a blood analyzer or other fluid analysis medical device. The waste container includes a flexible waste bag having a gas vent that may include a gas permeable, but substantially fluid impermeable, material or fabric. The fabric allows gases to escape the waste bag, but substantially prevents fluids from escaping. The waste container also includes a moisture absorbent material, such as a polyacrylamide polymer, that converts waste fluid, such as blood, from the blood analyzer into a substantially solid material, such as a gel, as waste fluids enter the waste bag. As waste fluids enter the waste bag and are converted into a substantially solid material, expelled gases that form in the waste bag as well as gases entering the waste bag from the blood analyzer pass through the gas vent. The waste container can be used with a blood analyzer that analyzes blood gases and electrolytes.

14 Claims, 2 Drawing Sheets

WASTE CONTAINER FOR PORTABLE BLOOD ANALYZER

RELATED APPLICATIONS

This application is related to co-pending U.S. patent application Ser. No. 08/650,340, entitled "Integral Fluid and Waste Container for Blood Analyzer;" U.S. patent application Ser. No. 08/650,341, entitled "Portable Modular Blood Analyzer with Simplified Fluid Handling Sequence;" U.S. patent application Ser. No. 08/650,622, entitled "Blood Gas/Electrolyte Calibrator and Method for Use;" U.S. patent application Ser. No. 08/650,465, entitled "Reference Solution Container for Blood Gas/Electrolyte Measuring System;" U.S. patent application Ser. No. 08/648,692, entitled "Locking Sensor Cartridge with Integral Fluid Port, Electrical Connections, and Pump Tube"; U.S. patent application Ser. No. 08/649,009, entitled "Sensors with Subminiature Through Holes and Method for Fabricating Such Sensors;" U.S. patent application Ser. No. 08/648,675, entitled "Electronic Wiring Substrate with Subminiature Through Holes and Method for Fabricating Such Sensors," U.S. patent application Ser. No. 08/648,676, entitled "A Sensor Cartridge for an Analyte Analyzer;" U.S. patent application Ser. No. 08/648,694, entitled "Method and Apparatus for Drilling Subminiature Through Holes in a Sensor Substrate;" and U.S. patent application Ser. No. 08/649,525, entitled "Method and Apparatus for Ratiometric Measurement of Hematocrit," which are all assigned to the assignee of the present invention.

BACKGROUND OF THE INVENTION

1. Field of the Invention

This invention relates to a waste container used in a medical device. More particularly, the present invention relates to a flexible container for holding waste fluids from a portable blood analyzer.

2. Description of Related Art

Blood analysis machines are used widely in the medical field to analyze various properties in human blood. (For convenience, the term "blood analyzer" will be used throughout this description to refer to blood analysis machines. It should be recognized, however, that the present invention is not intended to be limited to blood analyzers and can be used in urine, mucous, spinal fluid, and sperm analysis machines.) A blood sample is taken from a patient, and the blood is transferred into the blood analyzer. The blood analyzer is then used to determine the levels of particular elements (e.g., blood gases and electrolytes) found within the blood.

Conventional blood analyzers are large and heavy. They are therefore generally permanently located within a dedicated laboratory within a hospital or clinic. Blood samples taken from patients are brought to the blood lab where they are submitted to analysis by the blood analyzer.

There is a movement in the medical industry to reduce the size and weight of blood analyzers so that they can be brought to the patient, instead of the patient's blood sample being brought to the blood analyzer. The portability of blood analyzers introduces a potential problem. When the blood analyzer has finished analyzing a blood sample, the waste blood is transferred to a waste container connected to the blood analyzer. Moreover, calibrant fluids used to calibrate as well as to flush the blood analyzer after a blood sample is analyzed are also transferred to the waste container. Thus, a significant amount of fluid is transferred to the waste container. Because portable blood analyzers are moved around in a hospital or clinic to the patient, the waste containers in such analyzers must be designed such that they prevent waste fluids (especially potentially hazardous waste blood samples) from leaking or spilling out of the blood analyzer. Conventional waste bags are not designed, however, to prevent leakage and spillage.

In addition, a waste container for a portable blood analyzer should be light-weight and compact. The waste container should also be disposable and replaceable.

Therefore, a need exists for a waste container for a portable blood analyzer that is disposable, light-weight, and compact, and that substantially prevents spilling and/or leaking of waste fluids from the waste container. The present invention provides such a waste container.

SUMMARY OF THE INVENTION

The present invention is a waste container for a blood analyzer. The waste container of the present invention is flexible, expandable, and disposable. In addition, the waste container of the present invention is designed to substantially prevent spillage or leakage of waste fluids from the waste container. It should be recognized, however, that the present waste container is not limited to blood analyzers, but rather can be used in any medical device designed to hold waste fluids.

In accordance with the present invention, a disposable waste container for a portable blood analyzer is provided that protects against dangerous spillage or leakage of waste blood and other waste fluids and that is compact and light-weight. The waste container of the present invention includes a flexible waste bag that has a gas vent. Preferably, when the flexible waste bag is properly positioned in the portable blood analyzer, the gas vent is located near the top of the waste bag. Preferably, the vent includes a gas-permeable material (or patch) that is resistant to the passage of fluid through the patch. The patch allows gases (such as air) to escape the flexible waste bag. At the same time, however, the patch substantially prevents fluids (such as waste blood) from escaping the waste bag. Finally, the waste container of the present invention includes a polymeric moisture absorbent material that converts waste fluid (such as blood) from the portable blood analyzer into a substantially solid material (preferably a gel) as waste fluid enters the waste bag.

The details of the preferred embodiment of the present invention are set forth in the accompanying drawings and the description below. Once the details of the invention are known, numerous additional innovations and changes will become obvious to one skilled in the art.

DETAILED DESCRIPTION OF THE INVENTION

Throughout this description, the preferred embodiment and examples shown should be considered as exemplars, rather than as limitations on the present invention.

Figure 1:
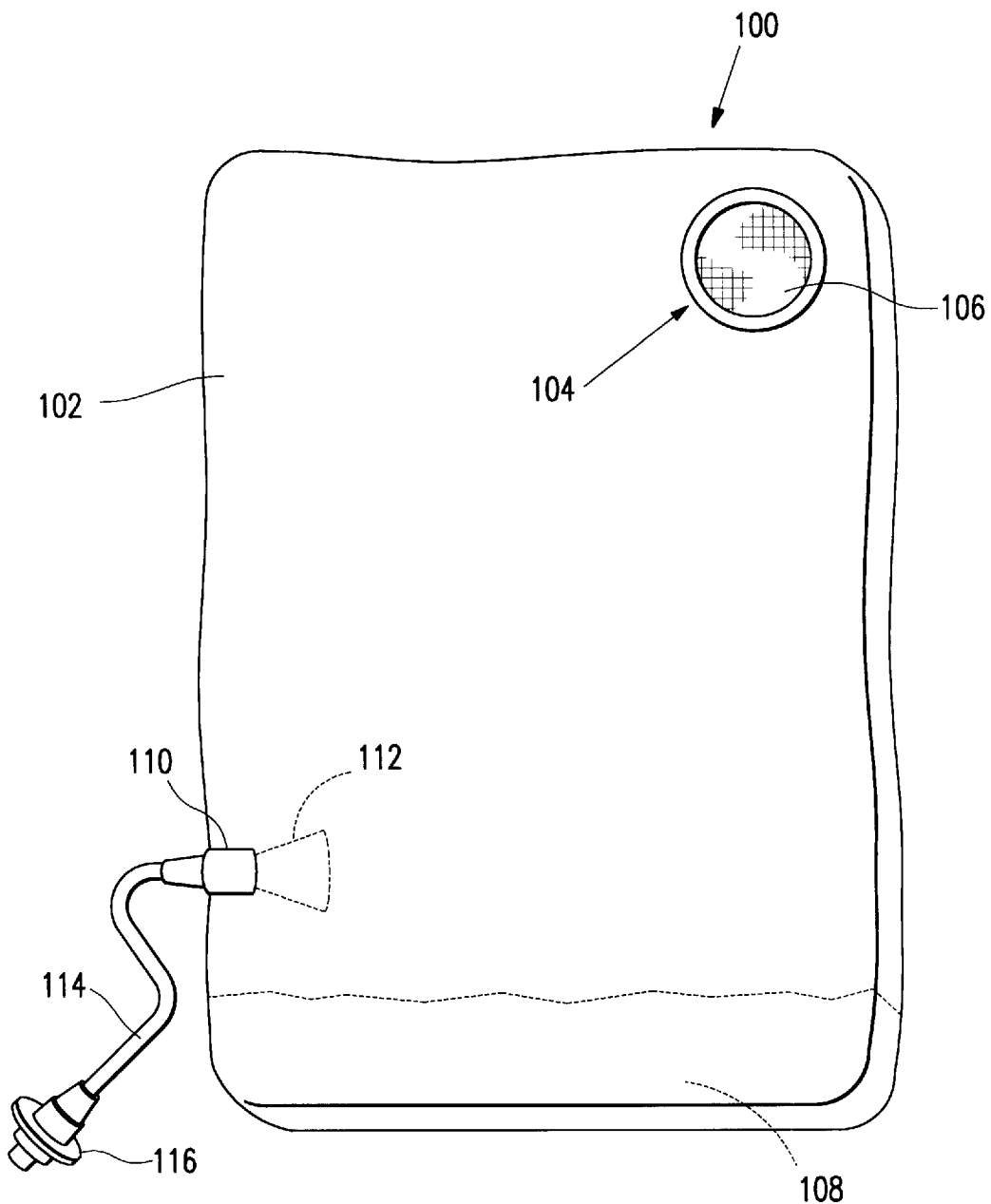
FIG. 1 is a perspective view of the waste container of the present invention.

FIG. 1 is perspective view of the preferred embodiment of the waste container 100 of the present invention. The waste container 100 includes a flexible waste bag 102 having a gas vent 104. Preferably, the waste bag is flexible and can expand as waste fluid enters the waste bag. In this way, the waste bag is extremely compact when empty, but can greatly expand in volume when it is full of waste fluids. The gas vent 104 illustrated in FIG. 1 is substantially circular and approximately 0.5 to 2 inches in diameter. It should be understood, however, that the gas vent 104 can be any shape and can be different sizes, provided it is sufficiently large to permit gases to effectively escape the waste bag 102. Similarly, it should be recognized that the waste bag 102 could have multiple gas vents.

The gas vent 104 preferably includes a material (or patch) 106. The patch 106 is gas permeable, but substantially prevents the passage of fluids. Thus, patch 106 permits gases to escape the flexible waste bag 102, but, at the same time, substantially prevents fluids from escaping. Preferably, the patch 106 is made from V-1200 Versapor R membrane from Gelman Sciences, a commercially available gas-permeable, substantially fluid-impermeable, material. It should be recognized, therefore, that any material that has gas-permeable pores that resist the passage of fluids can be used for the gas vent 104.

The waste container 100 also includes a moisture absorbent material 108. Preferably, the moisture absorbent material 108 is a finely crystalline or solid material, which converts fluids into a substantially solid material (preferably, a gel) when the fluids come into contact with the crystals. The preferred class of crosslinked moisture absorbent materials are polymers known as polyacrylamides. Alternate hydrophilic polymers include PHEMA (polyhydroxyethyl methacrylate), polyvinyl alcohol, cellulose, natural starch, polyvinylbutyral, polyethyleneoxide, and polyethyleneoxide-polypropyleneoxide block copolymers. These may be prepared with different molecular weights and may use mixtures of polymers, oligomers, and monomers to maximize the swelling ratio. All of these will absorb free water, swell to form a gel of varying stiffness, minimize interactions of blood components with the vent 104, and prolong the use life of the bag 102 to an acceptable period of several weeks or more. As an alternative to the moisture absorbent material, a desiccated sponge (or several pieces of desiccated sponge) could be used in the waste container 100 to absorb moisture.

Figure 2:
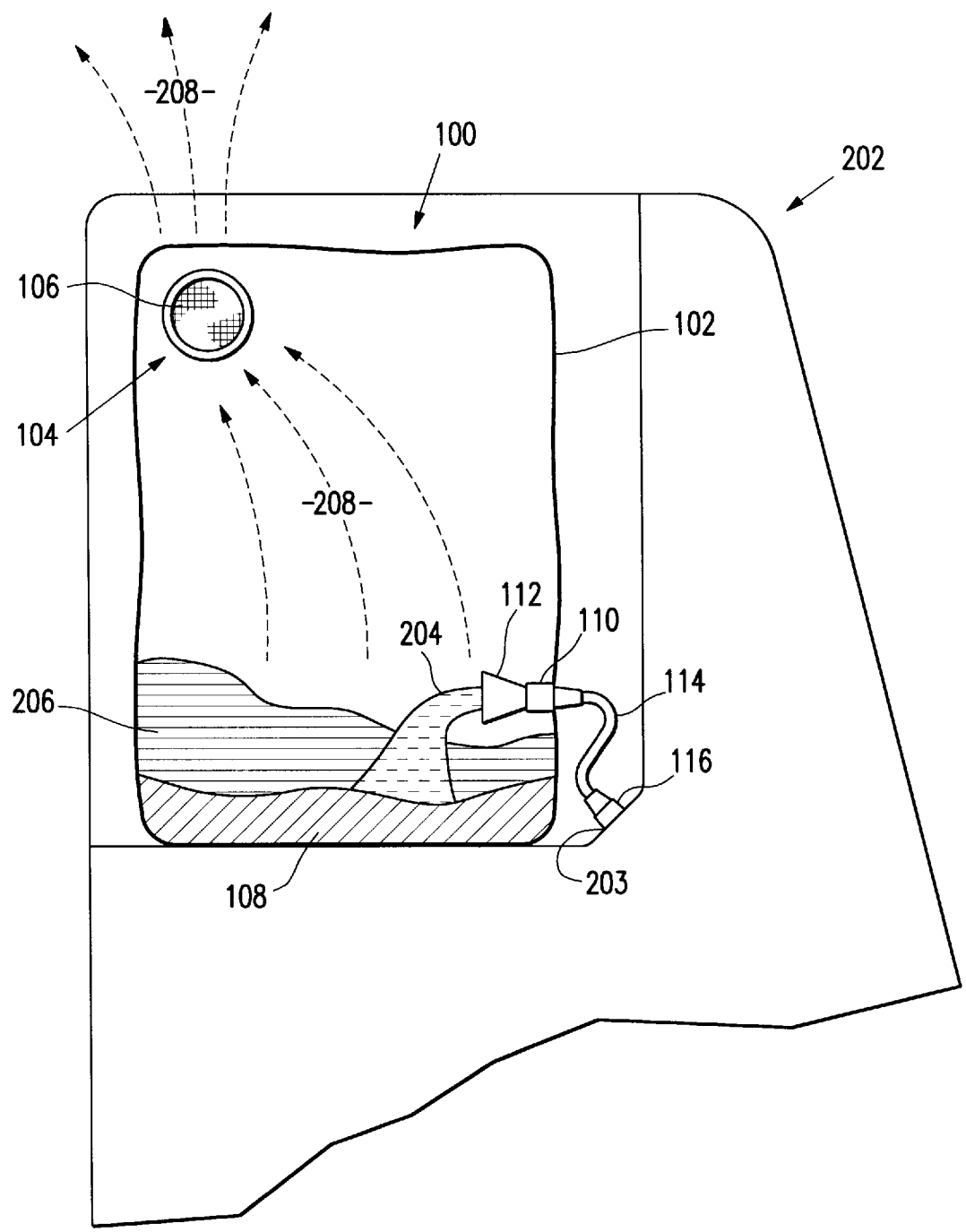
FIG. 2 is a perspective view of the waste container of the present invention, illustrating how waste fluid entering the waste bag is converted into a solid material and how gases are expelled through the gas vent on the waste bag.

FIG. 2 is a cut-away of the waste container 100 of the present invention within a portable blood analyzer 202, showing how the waste bag 102 expands and expels gases through the gas vent 104 as waste blood (or other waste fluids such as calibrant fluids) 204 enter the waste bag 102. A blood sample is taken from a patient and placed in the blood analyzer 202. Sensors in the blood analyzer 202 then analyze the blood sample and, when the analysis is complete, disposes of the blood sample into the waste bag 102 through an inlet port 110, which engages a fluid fitting 203 on the blood analyzer 202.

The inlet port 110 preferably includes a self-sealing valve that substantially seals the waste bag 102 against the escape of fluids when the inlet port 110 is disengaged from the fluid fitting 203. Moreover, when the inlet port 110 and fluid fitting 203 are engaged, the valve within the inlet port 110 prevents any appreciable flow of fluid out of the waste bag 102 and back into the blood analyzer 202. Preferably, the inlet port 110 includes a one-way or "anti-reflux" valve 112 that allows fluids and gases into the waste bag 102, but prevents any appreciable amount of fluid or gases from escaping the waste bag 102 through the inlet port 110. Pressure from fluids and/or gases present in the waste bag 102 maintains the anti-reflex valve closed against the flow of fluids back through the inlet port 102, as is known. Tubing 114 coupling the inlet port 110 to the blood analyzer 202 may have an additional one-way valve 116 that also prevents any appreciable fluid flow through the tubing 114 from the waste bag 102 to the blood analyzer 202. This additional valve 116 is preferably a Vernay Laboratories Duckbill Checkvalve No. VL1300-213.

After analysis of the blood sample is complete, calibrant fluid is used to flush the analyzer's sensor chamber and is also dispensed into the waste bag 102. Air (or other gases) is pumped through lines in the blood analyzer 202 to clean the calibrant fluid from the lines. Substantially all of the air is also dispensed into the waste bag 102. As blood samples and flushing calibrant fluids are dispensed into the waste bag 102, they come into contact with the moisture absorbent crystals 108 within the bag 102.

As the waste fluids 204 contact the moisture absorbent crystals 108, the crystals respond readily to convert the waste fluids 204 from a fluid state into a substantially solid state, such as a gel 206. As more waste fluids 204 and air enter the waste bag 102, the fluids 204 are converted into a gel 206 at the bottom of the waste bag 102, and the air (and other gases) 208 percolate through the gel towards the top of the waste bag 102. As a result, the air and gases 208 can be expelled through the vent 104. This prevents the waste bag 102 from bursting when a significant amount of gas is within the waste bag 102.

It can thus be seen that the waste container 100 of the present invention substantially reduces the risk of leaking or spilling of waste fluids 204 produced by the blood analyzer 202. First, the waste fluids 204 are contained in the bottom of the waste bag 102, while the gas vent 104 (the only opening, beside the inlet port 110, in the waste bag 102) is located substantially near the top of the waste bag 102. Second, the fluid resistant patch 106 substantially prevents any waste fluids from escaping through the gas vent 104, in the event waste fluids 204 were to come into contact with the gas vent 104. Third, because the moisture absorbent crystals 108 convert the waste fluids 204 into a solid or a substantially solid material or gel 206, the congealed fluids are far less likely to leak out through a flaw in the sealing of the bag 102. This reduces the possibility of spillage of waste fluid, which may contain various hazardous materials.

There is an additional reason for converting the waste fluids 204 into a gel 206 in a portable blood analyzer. Blood, even when diluted, clots and can easily clog the gas vent 104 in the waste bag 102. This problem is even more likely when the vent 104 includes a gas permeable patch 106, because such patches can easily become clogged with clotted blood. Therefore, the conversion of waste fluids into a substantially solid material reduces the potential for clotting and clogging of the gas vent 104 and thereby reduces the risk of the waste bag 102 bursting due to increasing pressure caused by gases within the waste bag 102.

As can be seen in FIG. 2, when the waste container 100 is normally positioned within the blood analyzer 202, the inlet port 110 and moisture absorbent material 108 are located at or near the bottom of the waste bag 102. This maintains the waste fluids 204 at the bottom of the waste bag 102 and reduces the chances of the waste fluids contacting the gas vent 104 when the bag 102 is partially collapsed. The gas vent 104 is the only opening in the waste bag 102 (beside the inlet port 110, which is a sealable valve that prevents fluid flow out of the bag 102) and is located substantially near the top of the waste bag 102. The absorbent material 108 acts as a barrier to keep the gas vent 104 from being exposed to waste fluids that would otherwise clog the gas vent 104. The vent 104 will remain functional for many weeks after the first fluid waste sample is transferred into the bag 102.

Testing has been performed to confirm the operating dynamics of the waste container 100. The waste container 100 was tested for volumetric expansion, drop tests, and air vent function.

The waste bag used in testing is designed to hold a maximum of 2000 ml. The expected volume from regular use is between 1100 and 1200 ml. In the test, air was intermittently injected into the waste bag as it was filled with 1200 ml of water. The polyacrylamide crystals absorbed the solution immediately as it entered the bag. The injected air percolated through the gel mixture and vented through the patch. The solution did not flow back through the check valves. Once filled, a one inch hole was cut into the corner of the bag to stimulate a seam failure. The gel mixture was sufficiently solidified to prevent all but a few drops of liquid to escape. Other filled bags were dropped onto hard surfaces to simulate extreme handling situations. None of the bags leaked due to the material and compliant contents.

A 40 to 1 ratio of solution to absorbent crystals was specifically chosen in this application to optimize both leak prevention and volumetric expansion. A higher percentage of crystals causes the bag to expand 10% more than that of the original components. Expansion volume is important, because the components are contained in a closed system (i.e., in the bag). A lower percentage of absorbent material was found to inadequately absorb the waste fluids and thus increase the risk of contamination.

The waste bags have been successfully tested in a stimulated clinical environment. The bags were tested daily for one month. There were no indications of air vent blockage or fluid leaks.

A number of embodiments of the present invention has been described. Nevertheless, it will be understood that various modifications may be made without departing from the spirit and scope of the invention. For example, the waste bag 102 could be made from a plastic material (e.g., a PVC film), but it can also be made from any other material that is flexible and has the ability to expand in volume as it fills with waste fluid, such as any gas-permeable, substantially fluid-impermeable, material, and, even more broadly, any plastic sheet or polyester that can be heat sealed together. Further, the waste container 100 of the present invention has been illustrated and explained with a single gas vent 104. It should be recognized, however, that the waste container 100 of the present invention can have several gas vents positioned in various locations on the waste container. Accordingly, it is to be understood that the invention is not to be limited by the specific illustrated embodiment, but only by the scope of the appended claims.

What is claimed is:

1. A waste container for an analyzer for analyzing bodily fluids, comprising:
   a. a flexible waste bag that prevents any appreciable amount of fluid from escaping, coupled to the analyzer by an inlet port that engages a fluid fitting on the analyzer, for receiving waste fluid from the analyzer, the flexible waste bag having a gas vent that allows gases but not any appreciable amount of fluid to escape the flexible waste bag;
   b. a moisture absorbent material contained in the waste bag for converting waste fluid received from the analyzer into a solid material, thereby causing the waste bag to expand as the waste fluid is converted within the waste bag; and
   c. a self-sealing valve that seals the flexible waste bag against the escape of fluids when the inlet port is disengaged from the fluid fitting.

2. The waste container of claim 1 wherein the moisture absorbent material converts the liquid waste into a gel.

3. The waste container of claim 2 wherein gases percolate through the gel and are forced through the patch covering the gas vent as waste fluid enters the waste bag.

4. The waste container of claim 1 wherein the vent includes a gas-permeable and fluid-impermeable material.

5. The waste container of claim 1 wherein the waste bag has a top and a bottom and wherein the waste fluid enters the waste bag from an opening in the bottom of the waste bag and the gas vent is located at the top of the waste bag.

6. The waste container of claim 1 wherein the analyzer is a blood analyzer and the waste fluid is blood.

7. The waste container of claim 6 wherein the moisture absorbent material converts the blood into a gel to substantially prevent the blood from clotting and clogging the gas vent.

8. The waste container of claim 5 wherein the opening in the bottom of the waste bag is an inlet port including an anti-reflux valve.

9. The waste container of claim 7 wherein the analyzer is a portable blood analyzer.

10. The waste container of claim 1 wherein the moisture absorbent material is a polyacrylamide polymer.

11. A waste container for a portable blood analyzer, comprising:
    a. a flexible waste bag that prevents any appreciable amount of fluid from escaping, coupled to the portable blood analyzer by an inlet port that engages a fluid fitting on the analyzer, for receiving waste fluid from the portable blood analyzer, the flexible waste bag having a gas vent for allowing gases but not any appreciable amount of fluid to escape the flexible waste bag;
    b. means, contained in the waste bag, for converting waste blood from the portable blood analyzer into a gel as waste blood enters the waste bag, thereby causing the waste bag to expand as the waste fluid is converted within the waste bag; and
    c. a self-sealing valve that seals the flexible waste bag against the escape of fluids when the inlet port is disengaged from the fluid fitting.

12. The waste container of claim 11, further comprising:
    a. a one-way valve for allowing fluids to enter the waste bag and for preventing fluids from exiting the waste bag through the valve.

13. A disposable waste container for a blood analyzer, comprising:
    a. a flexible expandable waste bag that prevents any appreciable amount of fluids from escaping, coupled to the blood analyzer by an inlet port that engages a fluid fitting on the analyzer, having a top and a bottom when the waste bag is properly positioned in the blood analyzer and having an inlet port located at the bottom of the waste bag and a gas vent located at the top of the waste bag;
    b. a moisture absorbent material contained in the waste bag for converting waste blood from the portable blood analyzer into a gel, thereby causing the waste bag to expand as waste blood enters the waste bag through the inlet port and is converted within the waste bag;
    c. the gas vent including a gas-permeable and fluid-impermeable material for allowing gases but not any appreciable amount of fluid to escape the waste bag; and
    d. a self-sealing valve that seals the flexible waste bag against the escape of fluids when the inlet port is disengaged from the fluid fitting.

14. The disposable waste container of claim 13 wherein gases are expelled through the gas vent as waste blood and air enters the waste bag.

* * * * *